United States Patent
Sheffer et al.

(10) Patent No.: US 10,552,931 B2
(45) Date of Patent: Feb. 4, 2020

(54) AUTOMATED CLINICAL INDICATOR RECOGNITION WITH NATURAL LANGUAGE PROCESSING

(71) Applicant: A-Life Medical, LLC, San Diego, CA (US)

(72) Inventors: Ronald Sheffer, Brookline, MA (US); Mark Morsch, San Diego, CA (US); Michelle Wieczorek, Waterford, PA (US)

(73) Assignee: OPTUM360, LLC, Eden Prairie, MN (US)

( * ) Notice: Subject to any disclaimer, the term of this patent is extended or adjusted under 35 U.S.C. 154(b) by 629 days.

(21) Appl. No.: 14/019,489

(22) Filed: Sep. 5, 2013

(65) Prior Publication Data

US 2015/0066537 A1    Mar. 5, 2015

(51) Int. Cl.
*G06Q 50/22* (2018.01)
*G06Q 10/10* (2012.01)

(52) U.S. Cl.
CPC .............. *G06Q 50/22* (2013.01); *G06Q 10/10* (2013.01)

(58) Field of Classification Search
CPC .......... G06Q 50/22; G06Q 50/24; G06Q 10/10
See application file for complete search history.

(56) References Cited

U.S. PATENT DOCUMENTS

| | | |
|---|---|---|
| 6,915,253 B1 | 7/2005 | Chapman |
| 6,915,254 B1 | 7/2005 | Heinze et al. |
| 7,260,480 B1 * | 8/2007 | Brown ................. G06F 19/324 700/1 |
| 7,493,253 B1 | 2/2009 | Ceusters et al. |
| 7,908,552 B2 | 3/2011 | Heinze |
| 7,949,538 B2 | 5/2011 | Heinze |

(Continued)

FOREIGN PATENT DOCUMENTS

| | | |
|---|---|---|
| WO | 2004055783 A2 | 7/2004 |
| WO | 2006014845 A2 | 2/2006 |

(Continued)

OTHER PUBLICATIONS

"Supercharged CDI: NLP, intelligent workflow and CAC revolutionize CDI program at UPMC", OPTUM, Mar. 2013. (6 pages).*

(Continued)

*Primary Examiner* — Robert A Sorey
*Assistant Examiner* — Kristine K Rapillo
(74) *Attorney, Agent, or Firm* — Dorsey & Whitney, LLC

(57) ABSTRACT

Computer-based, natural language processing systems and methods are provided for review of clinical documentation and other medical records, and for clinical documentation improvement. The systems and methods are configured to review documents in the record using a natural language processor and to identify clinical indicators with associated contextual information. The clinical indicators are compared to scenarios to generate markers based on an information model. The markers used to generate physician queries and other informational requests with supporting evidence for each query based on indicators identified in the record. In additional examples, pragmatic guidelines including business-based rules can also be utilized, either in combination with, or as part of, the scenarios in the information model.

19 Claims, 6 Drawing Sheets

(56) References Cited

U.S. PATENT DOCUMENTS

| | | | |
|---|---|---|---|
| 8,423,370 B2 | 4/2013 | Heinze | |
| 8,548,795 B2* | 10/2013 | Anisimovich | G06F 17/2755 704/2 |
| 8,655,668 B2 | 2/2014 | Heinze | |
| 8,682,823 B2 | 3/2014 | Heinze et al. | |
| 8,731,954 B2 | 5/2014 | Heinze et al. | |
| 8,898,798 B2* | 11/2014 | Rogers | G06F 19/32 726/26 |
| 2004/0117206 A1 | 1/2004 | Steinberger et al. | |
| 2005/0137910 A1 | 6/2005 | Rao et al. | |
| 2006/0020444 A1 | 1/2006 | Cousineau et al. | |
| 2006/0020447 A1 | 1/2006 | Cousineau et al. | |
| 2006/0020465 A1 | 1/2006 | Cousineau et al. | |
| 2006/0020466 A1 | 1/2006 | Cousineau et al. | |
| 2006/0020492 A1 | 1/2006 | Cousineau et al. | |
| 2006/0020493 A1 | 1/2006 | Cousineau et al. | |
| 2007/0226211 A1 | 9/2007 | Heinze et al. | |
| 2008/0004505 A1 | 1/2008 | Kapit et al. | |
| 2008/0256329 A1 | 10/2008 | Heinze et al. | |
| 2009/0070140 A1 | 3/2009 | Morsch et al. | |
| 2011/0167074 A1 | 7/2011 | Heinze et al. | |
| 2011/0307521 A1 | 12/2011 | Slezak et al. | |
| 2012/0014559 A1 | 1/2012 | Suehling et al. | |
| 2012/0060216 A1* | 3/2012 | Chaudhri | G06F 19/322 726/21 |
| 2012/0212337 A1 | 8/2012 | Montyne et al. | |
| 2012/0239671 A1 | 9/2012 | Chaudhri et al. | |
| 2012/0278102 A1 | 11/2012 | Johnson | |
| 2013/0006653 A1 | 1/2013 | Mills | |
| 2014/0019160 A1* | 1/2014 | Loya, III | G06Q 50/22 705/3 |
| 2014/0129803 A1 | 5/2014 | Heinze et al. | |
| 2014/0257842 A1 | 9/2014 | Heinze et al. | |
| 2014/0337044 A1 | 11/2014 | Heinze | |

FOREIGN PATENT DOCUMENTS

| | | |
|---|---|---|
| WO | 2006014846 A2 | 2/2006 |
| WO | 2006014847 A2 | 2/2006 |
| WO | 2006014851 A1 | 2/2006 |
| WO | 2012122122 A1 | 9/2012 |

OTHER PUBLICATIONS

Department of Health and Human Services, "HIPPA Administrative Simplifications: Modification to Medical Data Code Set Standards to Adopt ICD-10-CM and ICD-10-PCS", Federal Register vol. 74, No. 11, Jan. 16, 2009/Rules and Regulations. (35 pages).

Robert E. Nolan Company, "Replacing ICD-9-CM with ICD-10-CM and ICD-10-PCS: Challenges, Estimated Costs and Potential Benefits", Simsbury, CT, Robert E. Nolan Company, Oct. 2003. (39 pages).

"Using Coding Automation to Aid the Transition to ICD-10", Educational Report Sponsored by Optum, HFMA, Nov. 2011, pp. 1-8. (8 pages).

Johnson, Kerry, "Revenue Cycle Strategist: Implementing ICD-10: A Canadian Perspective from the Front Line", Healthcare Financial Management Association, Feb. 2009. (8 pages).

Libicki, et al., "The Costs and Benefits of Moving to the ICD-10 Code Sets", RAND Corporation Mar. 2004, Santa Monica, CA. (85 pages).

Morsch, Mark, "Advanced coding technology to advance the revenue cycle, Natural language processing with LifeCode", OptumInsight, Eden Prairie, MN, 2011. (4 pages).

Morsch, Mark, "Better technology leads to better coding", Optum, Eden Prairie, MN (2012). (4 pages).

International Search Report & Written Opinion for PCT/US2014/054329 dated Feb. 3, 2015. (13 pages).

"Optum & UPMC collaborate to launch CDI Module within Enterprises Computer-Assisted Coding Platform", OptumInsight, Apr. 27, 2012, retrieved Jan. 21, 2015 from https://www.youtube.com/watch?v=D9f0ZxxPNxm. (1 page).

Endicott, M., "Innovations in CDI Automation", ICD TEN Top Emerging News, May 2013. (2 pages).

Mark Morsch et al: "Transitioning to ICD-10: Why You Can Trust NLP Technology with ICD-10 Coding", California Health Information Association 2013 Convention & Exhibit, Jun. 11, 2013, pp. 1-30.

Heja et al: "Galen based formal representation of ICD10", International Journal of Medical Informatics, Elsevier Scientific Publishers, Shannon, IR, vol. 76, No. 2-3, Feb. 10, 2007, pp. 118-123.

International Search Report and Written Opinion dated Feb. 4, 2015 for PCT Patent Application No. PCT/US2014/058538. (12 pages).

Gergely: "Galen based formal representation of ICD10", International Journal of Medical Informatics, Elsevier Scientific Publishers, Shannon, IR, vol. 76, No. 2-3, Feb. 10, 2007, pp. 118-123.

Mullin, Robert , "A brief History of ICD-10-PCS", Journal of AHIMA, 1999, vol. 70 No. 9 pp. 97-98.

\* cited by examiner

AUTOMATED CLINICAL INDICATOR RECOGNITION WITH NATURAL LANGUAGE PROCESSING

BACKGROUND

This disclosure relates generally to clinical documentation and, specifically, to automated techniques for recognizing clinical indicators of disease. In particular, the disclosure relates to natural language processor techniques for clinical document review, including automated recognition of disease indicators.

Broadly speaking, clinical documentation improvement (CDI) initiatives seek to improve the quality of provider documentation in order to better reflect the services rendered and more accurately represent the complete patient encounter. CDI programs can benefit many clinical and administrative functions in healthcare delivery, including coding, quality measures reporting, care management, outcomes analysis, risk analysis, and subsequent care decisions. These benefits are derived from clearer and more complete clinical documentation.

CDI can play an important role in the transition to new medical classification and coding systems, for example ICD-10, ICD-11, and other revisions to the ICD medical classification system (International Statistical Classification of Diseases and Related Health Problems) by the World Health Organization. With greater specificity and increased scope for both diagnosis and procedure coding, CDI programs in provider organizations can address the potential gap between the content of current clinical documentation and the level of detail required for new and updated ICD codes.

Combining the existing opportunities to realize clinical and financial benefits with the magnitude of the ICD changes, providers seek new and more accurate solutions to help improve documentation. These solutions should be efficient, with minimal disruption to the physician workflow, and they should have specific, measurable benefits.

In this disclosure, computer-assisted natural language processing (NLP) technology is applied to transform existing CDI programs and coding solutions. Like coding, CDI programs can be labor intensive and require highly trained specialists to execute. CDI also has a unique set of challenges, because, while similar to coding in some respects, CDI requires a different approach to medical records review in order to identify potential gaps in the clinical story.

A high level of both clinical and processing knowledge is required to identify these clinical gaps and other improvement scenarios, with an advanced understanding of which areas have the greatest potential for development from both clinical and financial standpoints. With existing programs it is not possible to effectively review every chart and patient encounter in order to identify and select the greatest opportunities for improvement. Where physician queries must be communicated back to the provider, moreover, it is notoriously difficult to integrate this feedback into the provider workflow using standard communications mechanisms such as email and fax technology.

To transform existing CDI programs, more advanced technology should be applied to identify particular cases that exhibit opportunities for improvement in clinical care, provide structured models of clinical evidence to support consistent decisions by CDI staff, and incorporate new tools to improve construction of specific queries, more efficiently communicate these queries to clinicians, and monitor responses to improve key performance measures. This disclosure describes factors relevant to the alignment of NLP technology and CDI solutions to accomplish these goals, including: (1) more accurate extraction of clinical evidence from medical records for automated case-finding, (2) an improved clinical information model that supports consistent query decisions, and (3) compositional approaches to NLP, which can recognize more sophisticated CDI scenarios.

SUMMARY OF THE INVENTION

This application is directed to computer-based, natural language processing systems and methods for review of clinical documentation and other medical records and for clinical documentation improvement. The systems and methods are configured to review documents in the record using a natural language processor, and to identify clinical indicators with associated contextual information.

The clinical indicators are compared to scenarios to generate markers based on an information model. The markers are used to generate physician queries and other informational requests, with supporting evidence for each query based on indicators identified in the record. In additional examples, pragmatic guidelines including business-based rules can also be utilized, either in combination with, or as part of the scenarios in the information model.

DETAILED DESCRIPTION

Figure 1:
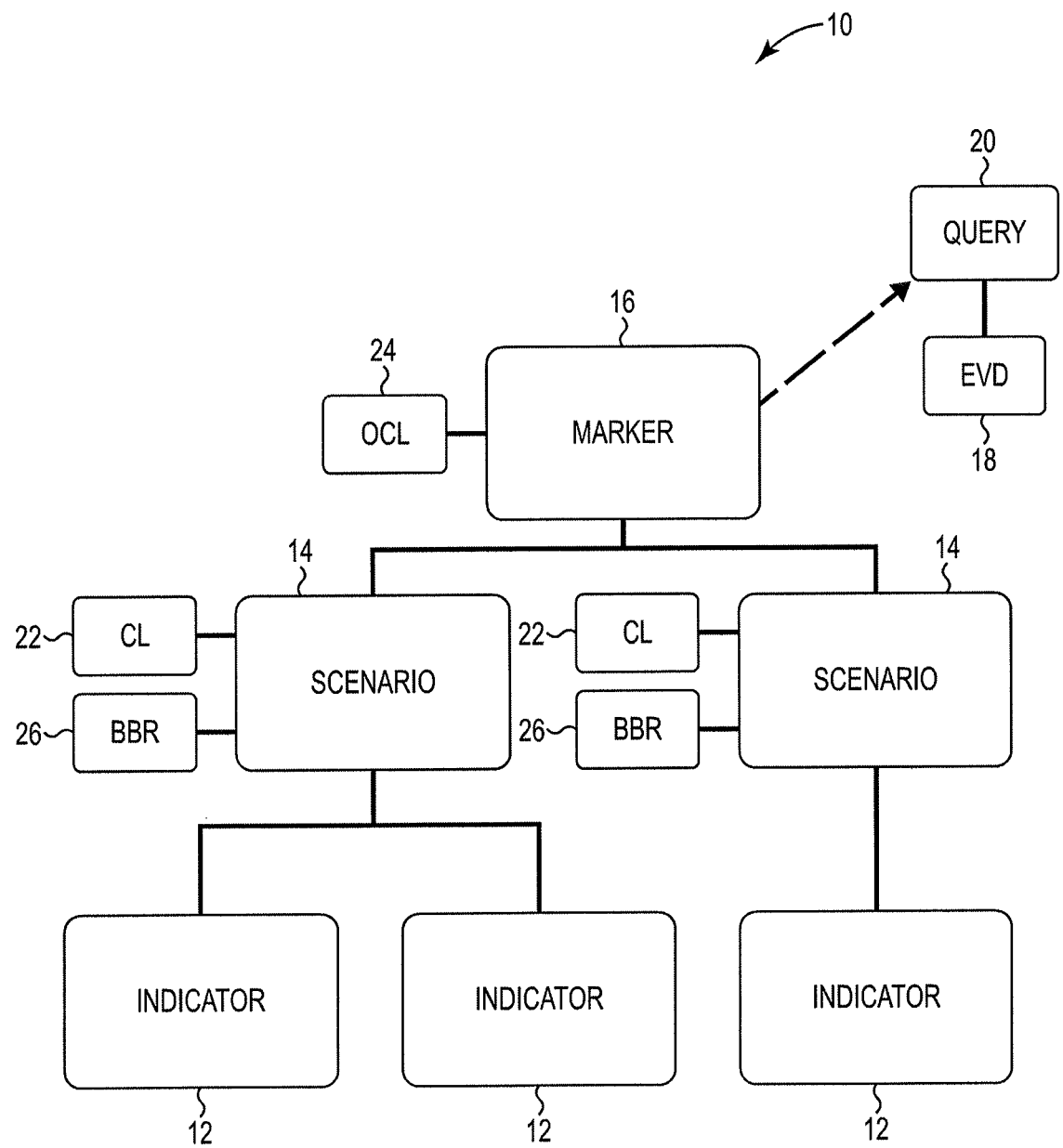
FIG. 1 is a block diagram of a clinical documentation improvement (CDI) information model, in a representative three-tier example.

To improve existing CDI programs, this disclosure describes techniques to amplify prior capabilities to find cases that exhibit improvement opportunities, provide structured models of clinical evidence to support consistent CDI decisions, and extend natural language processing (NLP) technology to capture clinical indicators from both unstructured and structured sources. Relevant features include, but are not limited to: (1) accurate extraction of clinical evidence from medical records, including both structured and unstructured sources using an extended NLP engine for automated case-finding; (2) a clinical (CDI) information model that supports consistent query decisions; and (3) a compositional model to fuse together information from different portions of a medical record, in order to recognize and act upon sophisticated CDI scenarios.

Natural language processing (NLP) can be applied to a number of areas in the healthcare industry, including text translation, document retrieval and routing, and information extraction. Relevant techniques including LIFECODE processor and other NLP engines are described, for example, in U.S. Pat. No. 6,915,254 to Daniel T. Heinze and Mark L. Morsch, AUTOMATICALLY ASSIGNING MEDICAL CODES USING NATURAL LANGUAGE PROCESSING, issued Jul. 5, 2005, and U.S. Pat. No. 7,908,552 to the same inventors, MERE-PARSING WITH BOUNDARY AND SEMANTIC DRIVEN SCOPING, issued Mar. 15, 2011, each of which is incorporated by reference herein, in the entirety. Additional relevant techniques are described in U.S. patent application Ser. No. 11/735,264, filed Apr. 13, 2007, MULTI-MAGNITUDINAL VECTORS WITH RESOLUTION BASED ON SOURCE VECTOR FEATURES, and U.S. patent application Ser. No. 12/185,754, filed Aug. 4, 2008, VISUALIZING THE DOCUMENTATION AND CODING OF SURGICAL PROCEDURES, each of which is also incorporated by reference herein, in the entirety.

In the area of clinical Documentation Improvement (CDI), natural language processing can be utilized by healthcare providers for reviewing and comparing medical records and coding, to find areas where documentation may be lacking in some way. Common reasons for documentation deficiencies are underspecified diagnoses or procedures, and missing diagnoses or procedures.

To find such deficiencies, the medical record is reviewed to identify indicators and other data such as statements (e.g., made by a physician, consultant, nurse, or physician assistant), lab values, medications (ordered or administered), specialist findings (e.g., radiology, pathology, cardiology), treatments, supplies, vital signs, etc., which are not in line with (not reflected in, or inconsistent with) what was documented in, and in the end coded from, the attending physician conclusions. Because attending physicians are ultimately responsible for the record, any such discrepancies are sent back to the provider in the form of a query. If the physician (or other responsible party) determines that something was missed or omitted, or not correctly documented in the medical record, a statement is supplied, and the record is amended to reflect the statement.

This disclosure provides for recognition of such documentation deficiencies by automatically extracting clinical indicators from both unstructured and structured medical text and other data in the record, using natural language processing. The disclosure also describes a data model of clinical information, which groups indicators into scenarios based upon expert knowledge or evidence-based criteria. Additional applications are not restricted to CDI, and could be used in other evidence-based analytics scenarios for improved healthcare management.

Without the right combination of relevant feedback, timing, and follow up, CDI programs can have mixed results. One improved approach to CDI is to educate providers regarding potential weaknesses in clinical documentation in areas that may be problematic from both a clinical and financial perspective. While education can be helpful, however, it can have greater impact when coupled with specifically identified examples of deficient documentation. This type of retrospective analysis and feedback influences future behavior and may be combined with auditing analysis to validate changes, so that healthcare organizations can develop more effective solutions to CDI.

In a proactive approach, CDI is applied to identify documentation with potential deficiencies concurrent with or immediately following patient stays. In this technique, requests or queries to the provider can be generated in near real time in order to help fill gaps in the clinical or treatment documentation at the point of care, or in short-term follow up. For example, documentation can be updated to fill gaps before discharge, during discharge, or soon after discharge. This type of CDI analysis can also be implemented to encompass CDI opportunities working on the floor, within or close to the patient care facility, and in teams of health information management (HIM) or care management specialists who can review records concurrently with the patient stay.

These forms of CDI analysis face some of the same challenges as medical coding, including limited time available to completely understand a large number of potentially complex medical records. Because many CDI opportunities involve correspondingly complex medical encounters, moreover, the demands are even greater to develop effective review techniques, identify potential improvements, and select appropriate solutions.

Cases for CDI review can also be selected based upon their potential fit to a given improvement scenario. For example, natural language processing can be applied to computerized CDI analysis, scanning or reading every chart or record to identify cases with a need for follow-up. Developing appropriate queries based upon evidence in the medical record also requires a broad-based clinical understanding of how the various pieces of diagnostic evidence fit together. Queries should be constructed to comply with the relevant organization's CDI policies.

Taken together, these challenges include identifying a sufficiently high percentage of opportunities within the record base, working efficiently and concurrently to improve care within a patient stay and during follow up, and adjusting to the demands of new coding systems, diagnostic tools, and other standards, including ICD-10. At the same time, consistently applying regulatory and organizational policies is also relevant, along with measuring physician query response rates and agreement levels, and developing new technology to help CDI professionals provide more efficiently, timely and cost effective clinical records review.

Automated Case Identification

Factors in developing this approach include the difficult technical challenges of case review and the associated problems of identifying cases that have a query opportunity. This disclosure enables the CDI natural language processing module to automate much of the CDI program in hospitals and clinical settings, including the discovery of cases that have documentation deficiencies. Typically, even with existing automated record retrieval, scanning and analysis systems, CDI specialists often still need to spend considerable time reviewing individual cases in order to find sufficient clinical evidence. For example, a CDI specialist may complete eight to twelve new reviews per day using existing techniques, along with twelve to twenty "re-reviews," for a total of twenty to thirty-two records per day for each CDI specialist. This is comparable to the level of productivity in inpatient coding, leading to the conclusion that the CDI staff would need to be similar in size to the coding staff in order to fully review every inpatient case for CDI opportunities. This does not take into account the concurrent nature of the CDI process, in which the same case might require both review to identify new opportunities and re-review for validation and to determine whether previously identified CDI opportunities have been addressed.

With automated case finding, the CDI module also provides for concurrent coding and physician query. For health information management systems, this provides an opportunity to code and address gaps, omissions and other issues or omissions in documentation with patient information to support coding efforts much earlier in the workflow—as opposed to post-discharge, as is the case in existing systems. For physicians and other care providers, this brings the questions related to patient care and supporting documentation to the forefront, allowing the provider to respond and sign off on information concurrently, as opposed to after discharge when documentation often needs to be revisited, in order to recall the important aspects of care provided to the patient.

This approach provides patient information and appropriate coding information sooner, allowing for better quality mapping and tracking of quality measures. More advanced CDI technology also provides for accurate reimbursement, improved coding, decreased time and labor for coding and follow up, better quality of care and improved patient safety. Additionally, the CDI techniques described here provide the ability to identify and address patient care issues earlier in the care and documentation processes, with a focus on enhancing the quality of care and improving the clinical documentation experience, for more efficient and cost effective healthcare management.

Using natural language processing (NLP), all electronic clinical documentation in the medical record associated with a case is scanned to look for information that points to a missing or underspecified diagnosis or procedures. The NLP engine is sensitive to additional contextual factors such as when an indicator was mentioned in the course of a hospital stay or course of treatment, negation data associated with the indicator, whether the indicator was recorded as under consideration or ordered, and how many times any particular indicator of indication is repeated throughout the case documentation. The NLP processing engine is also sensitive to where particular indicators come from (that is, what types of documents provide indicators, and what sections within those documents contain the indicators), and to who created the documentation (e.g., nurses, pathologists, radiologists, etc.). If relevant, the NLP engine can also consider whether any particular indicator is sensitive to other factors, such as the age or gender of the patient.

All the indicators identified in the medical record are reviewed, both separately and in combination, in order to determine whether enough information has been found to warrant review of the case. Groups of such indicators are called (or arranged into) scenarios, where each scenario points to a marker, which indicates a clinical condition that was possibly missed or underspecified in the documentation.

The scenarios and markers can also be assigned an associated confidence. The particular combination of indicators that is found yields a confidence level for the associated scenario, and the marker inherits the highest overall confidence level associated with the scenario. These techniques substantially improve upon previous CDI analysis, where specialized programs were utilized to look for missing or underspecified documentation in individual elements of the record. Here, the NLP engine reviews the entire record for bits of data and combinations of information, which indicate that other parts of the documentation may be lacking.

The NLP engine can review dozens of documents in the record contemporaneously, and if enough indicators and contextual information are found, in the right combination, a query can be generated for the attending physician (or other provider) to make a determination as to whether a particular diagnosis or other element of the record has been omitted, insufficiently documented, or is otherwise absent from the record. By providing associated evidence of any such omission or oversight along with the query, based on the indicators and other contextual data identified in the record, the NLP engine also delivers more exact information to the physician (or other decision maker), so as to make a more informed, accurate decision, and to amend or correct the record as appropriate.

Advanced CDI analysis can also leverage computer assisted coding (CAC) techniques to more fully automate the process of case finding and identification and to improve accuracy. Natural language processing can also boost CDI productivity by analyzing and abstracting the particular information needed to identify potential physician query scenarios, and to improve query formulation for increased effectiveness. Cases that match specific query scenarios, as identified by NLP analysis, can then be routed for CDI review. CDI specialists can review the results of NLP coding and abstraction in order to quickly find relevant information in the charts and other clinical or medical records, which are indicative of deficiencies in documentation.

In some aspects this is analogous to the transformation of coders to reviewers and auditors using related CAC techniques. But in CDI the problems are substantially different, and the solutions also vary not only in the specific types of information that are relevant, but also in the particular data structures and communications pathways necessary to implement them.

In CDI, analysis is not limited to finding only "code-able" facts, but also encompasses other clinically significant facts that are evidence of an information or documentation gap. Documentation gaps (or document gaps) can arise due to a variety of phenomena, including cutting and pasting procedures that bury new information within an otherwise redundant record, lack of sufficient information in caregiver notes (e.g., short typed and abbreviated doctor notes), documentation of symptoms that indicate a given medical condition rather than the condition itself, incorrect or omitted diagnosis (e.g., from a drop down or pick list selection) where indicators and other evidence indicate a scenario and marker for another diagnosis that is not present in the record, and gaps generated due to failure to communication with the doctor or other care provider workflow.

More generally, using NLP with high recall and precision capability allows the CDI process to deliver a high level of benefits. High recall NLP is able to capture relevant clinical facts, no matter where they are documented in the medical record, including facts that would easily escape prior techniques and even manual review. Lab results, medication orders, and progress notes can also be analyzed, even where the body of records may be extensive for any given inpatient stay, outpatient treatment, or other medical encounter.

Like the boost provided to case mix index (CMI) assignments due to more complete information capture with CAC, high recall NLP can yield similar benefits for CDI programs, including case identifications that were previously missed even in existing automated reviews. In addition, provider queries need not be generated for information that is already present in the chart or record, but would otherwise have been missed, and this is a relevant factor to consider in ensuring high response rates to queries.

High precision NLP based CDI analysis also reduces wasted time reviewing charts that do not have deficiencies, but where the relevant information could not be identified or effectively verified with previous techniques. High precision NLP based CID analysis also reduces or minimizes the false positive rate, making the CDI analysis more efficient, and more effective at specifically identifying cases with the greatest likelihood of a documentation deficiency.

Thus, the impact of well-crafted NLP techniques on case finding is potentially large, particularly as a greater portion of medical records are provided and maintained in electronic form. While many organizations across the industry have begun adopting CAC methods, however, there remains a need for more advance CDI automation programs that can more fully leverage the interfaces and data flows used for CAC, as applied to NLP processing for CDI analysis.

CDI Information Modelling

To produce beneficial results from CDI analysis, an organization should have well defined policies and audit programs to ensure that these policies are consistently applied. Clinical evidence from the relevant medical records should be abstracted and interpreted following standard guidelines. Automation of case finding using NLP can significantly benefit the process of finding individual pieces of clinical evidence, but interpretation is needed to combine the individual items of clinical evidence in order to form effective queries. To support such standardized interpretation, NLP technology and associated business-based analysis rules can use an information model, as shown in FIG. 1.

FIG. 1 is a block diagram of a representative CDI information model 10. In this particular example, CDI information model 10 has a three-tier configuration, with first tier (lower level) clinical indicators 12, second tier (middle level) CDI scenarios 14, and third tier (upper level) markers 16.

CDI information model 10 formally defines the relevant clinical evidence for a given chart or record, and how that evidence can be combined to identify query opportunities. In this three-tier information model, the lowest level (first tier) includes CDI indicators 12, which are individual pieces of clinical evidence. Examples of indicators 12 include, but are not limited to, symptoms, physical findings, medications, and laboratory results.

The middle level of CDI information model includes CDI scenarios 14, which are defined as logical combinations of indicators 12, which fit particular criteria used to identify or select query opportunities. One or more CDI markers 16 are located at the top level (third tier) of CDI information model 10. Each CDI marker 16 represents one or more scenarios 14, each of which may fit the clinical profile of a specific condition, based on information or indicators 12. If the condition represented by marker 16 is not documented in a patient's chart or clinical record, then marker 16 also provides evidence (EVD) 18 to support a physician query (PQ) or other data request 20.

Indicators 12 include various data fields and other characteristics incorporated into scenarios 14 and markers 16 such as indicator label, indicator type, and additional data such as protocode, finding or lab, vital, meds, or supplies with (full) inherited output. Protocodes and related characteristics can be selected from a group including, but not limited to: cause (e.g., of a condition or indicator), code (e.g., ICS or other), finding (e.g., by physician, lab, or other provider), history (e.g., of a condition or indicator), key phrase (e.g., found in medical record, and associated with condition or indicator), medication (prescribed, ordered or administered), procedure (ordered or administered), radiology result (including any form of medical image data and associated findings), or symptom (e.g., attributed to patient, or found in physician notes or other notes in the medical record).

Lab results and related characteristics can be selected from a group including, but not limited to, sodium level, glucose level, blood panel data including full blood count (FBC), white blood cell (WBC) count, bands, stabs, platelets and other blood data, other body fluid laboratory or diagnostic data, oxygen levels, ejection fraction, and other cardiovascular, laboratory, or diagnostic data. Vital signs (vitals) and related characteristics can be selected from a group including, but not limited to, temperature, blood pressure (systolic and diastolic), respiratory rate, and heart rate.

Scenarios 14 are based on groups of indicators, indicating the reason for a marker 16, and include various data field and other characteristics such as scenario label, a SNOMED nomenclature clinical term or concept ID, and confidence (or confidence level) 22. Markers 16 include data fields and other characteristics such as marker source (or CDI), marker label (condition or procedure), marker type (or type of marker), SNOMED representation and concept ID (e.g., simple or complex) and overall confidence level 24 (e.g., high medium or low, or a numerical value).

One example of particular CDI marker 16 is sepsis. There are multiple scenarios 14 that may fit the profile for sepsis, for example based on indicators 12 such the mention of urosepsis or bacteremia in combination with intravenous (IV) administration of dopamine. Another scenario 14 for sepsis is based on indicators 12 such as the administration of IV antibiotics in an intensive care unit (ICU), while a third scenario 14 could is based on indictors 12 including the mention of urosepsis or bacteremia in combination with a positive blood or urine culture. CDI information model 10 can also include additional features, such as a confidence level (CL) 22 to indicate how strongly each scenario 14 supports a given marker 16, for example in the middle level or tier of CDI information model 10, or an overall confidence level (OCL) 24 associated with marker 16, in the top level or tier of CDI information model 10.

Information model 10 provides a robust foundation for NLP-assisted CDI. In particular, information model 10 is extensible to accommodate additional markers 12, scenarios 14 and indicators 16, with various other features such as individual and overall confidence levels 22 and 24. Information model 10 can also be expressed in terms of business-based rules (BBR) 26, which can be applied to indicators 12 and other the information extracted by the NLP, or to additional information or indicators 12 identified by other CDI analysis, including CDI specialist review. With business rules 26 driven from a standardized model 10, for example, in combination with or as separately supported scenarios 14, interpretation of indicators 12 and other evidence can be more consistent, providing more focused, accurate, and effective queries and other information requests 20.

The NLP approach provides for high-accuracy verification of coding and other information in the medical record. Thus, where clinical indicators 12 and other contextual evidence in the record generate a scenario 14 for a marker 16 indicating an ICD code or other information should be present on the record, with sufficiently high confidence level 22 or 24, but the code or other information is not present, a query 20 can be produced, with evidence 18 including or based on the indicators 12 and context that generated the corresponding scenario 14 and marker 16. At the same time, if sufficient clinical evidence is identified to generate a scenario 14 but information corresponding the associated marker 16 is already present, not necessarily just in the coding data but anywhere in the medical record, then no query 20 may be necessary, and none may be generated.

Compositional NLP for CDI

A third factor to consider in the alignment of NLP and CDI analysis is the requirement placed upon the core NLP technology. Natural language processing is by definition focused on extracting information from narrative text, but NLP technology limited to only narrative text would not be as suitable for an advanced CDI application. With the increasing adoption of electronic health records, moreover, both structured and semi-structured data are important sources of clinical evidence for CDI analysis, including vital signs, laboratory results and medication orders. This means that for NLP to be more successful in CDI, the technology may include components to handle not only narrative text, but also other forms of structured, semi-structured data, and relatively unstructured data, for example a combination of standard text entries, images, diagnostic test results, and even informal data such as hand-written notes, sketches, and other forms of data available for machine processing and interpretation.

Another advantage of NLP as applied to CDI is the possibility of a more compositional approach. The scenarios that define particular CDI markers are formed by logical combinations of clinical indicators, but these indicators should also be recognized in the appropriate context, in order to furnish the most relevant and accurate queries. For example, one indicator of sepsis is the IV administration of antibiotics in an ICU, as described above. The setting for delivery of the medication (in the ICU) is an important component of this indicator, and the NLP techniques described here have the capability to recognize such clinical indicators in combination with settings and other indicators components, even when these components are not expressed in close proximity to one another, for example as expressed in the medical record.

Two additional, sophisticated capabilities of NLP-based CDI are pragmatics and discourse analysis. In particular, these capabilities not only are important in order to accurately apply coding guidelines for CAC applications, and they are also useful in the context of NPL techniques applied to CDI analysis.

Generally speaking, pragmatics is the study of how context contributes to meaning In clinical documentation, one of the key types of pragmatic information is the type of document on which a particular piece of information comes from, or where the information is found. The document type provides important information about the creator of the document, the purpose for creating the document (and placing in the clinical record), and how any information such a document should be interpreted, in the context of the broader record of interest.

Figure 2A:
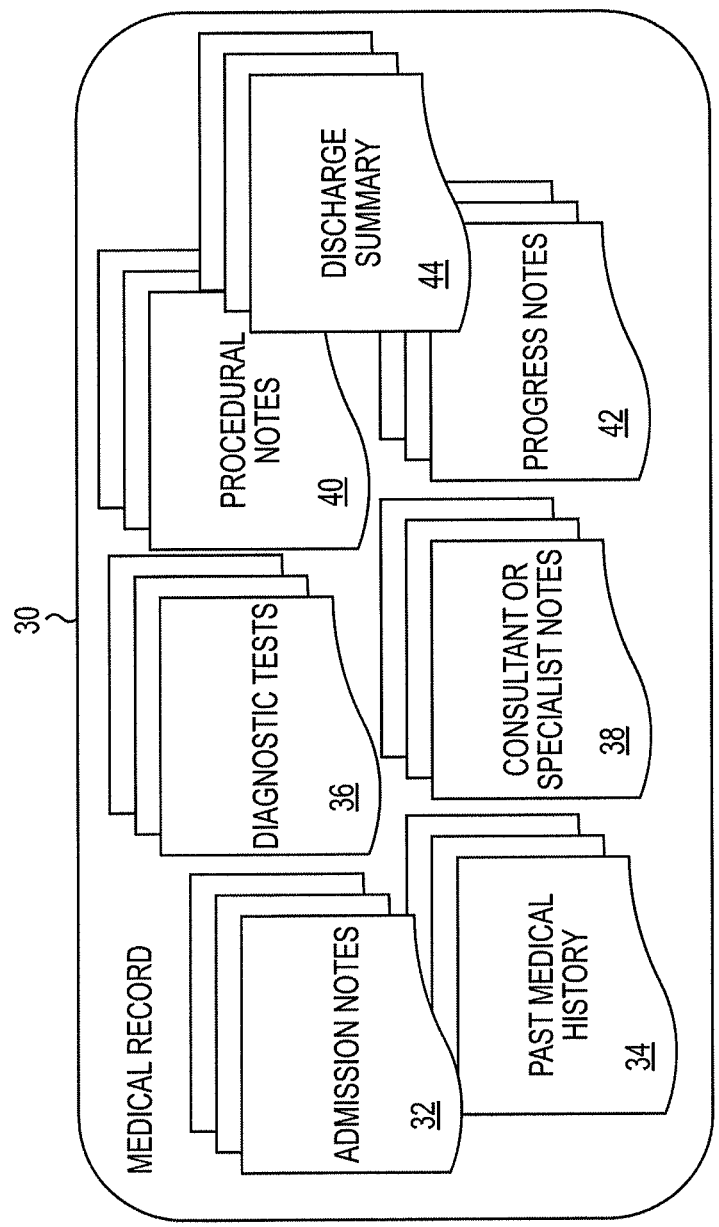
FIG. 2A is a block diagram illustrating representative documents in a medical record.

FIG. 2A is a block diagram illustrating representative documents that may frequently be found as part of a given medical record or clinical documentation 30. Such documents include, but are not limited to, admission notes 32, past medical histories 34, diagnostic tests 36, consultation or specialist notes 38, procedural notes 40, progress notes 42, and discharge summaries 44.

The particular documents illustrated in FIG. 2 are merely representative. In other examples, medical record 30 may also include blood tests and other lab tests, x-rays, computer-assisted tomography (CAT) and magnetic resonance imaging (MRI) scans and other images, electrocardiogram (ECG or EKG) and EEG (electroencephalogram) data, operating room notes (ORN), medical histories, observational notes, and other medical and clinical records and data. Medical record (or clinical documentation) 30 may also include additional or fewer categories of individual documents 32-44, and the documents and other data may be organized differently within the medical record 30.

Generally, medical record 30 may include both structured and unstructured data. Unstructured data includes free text, narratives, descriptions, notes, and summaries, as provided by the physician, or other caregiver, or even by the patient, for example in admission notes 32, histories 34, consultation or specialist notes 38, procedural notes 40, progress notes 42, and discharge summaries 44, or in the form of free text associated with imaging or diagnostics in diagnostic tests 36. Structured data has a more particular scheme and format, for example lab results, "pick-list" and drop down menu data selected from a limited number of fields. Diagnosis and treatments codes may also be considered structured data, as well as medication orders.

Business rules for CDI scenarios apply pragmatics to clinical indicators and other information in medical record 30, for example when the document type itself may be considered part of the indicator. For example, a statement of "lungs clear" on the interpretation of a chest x-ray (e.g., in diagnostic tests 36) is very different from a similar statement on a documentation of history and physical examination (H&P) document, for example in admissions notes 32, as opposed to past medical history 34, or in other parts of the record, such as consultation notes 38, procedural notes 40 or progress notes 42.

Pragmatics can also be relevant to CDI in considering the overall context for a given clinical indicator. In the case of something as apparently straightforward as hyponatremia, for example, a low sodium lab value may not really be enough information to decide whether a physician should be queried, and additional contextual information can also considered in order to decide whether a query for hyponatremia is relevant or necessary. Other conditions in the patient record (e.g., cirrhosis, congestive heart failure, nephrotic syndrome, massive edema, hypothyroidism, hypoglycemia, diabetes, etc.) can also play a role in serum sodium levels, as can other lab values.

For example, high glucose levels may correlate with lower sodium valuesd. Thus, one indicator may be based on a combination of different blood or other laboratory results, for example a low (or high) sodium level and a low (or high) glucose level, or using a formula to relate such laboratory results. Patient activity can also be relevant to the diagnosis of hyponatrema, and NLP can be utilized to consider such contextual factors when deciding whether to generate a physician query. For example, the New England Journal of Medicine reported that 13% of runners who finished the 2002 Boston Marathon were in a hyponatremic condition.

Figure 2B:
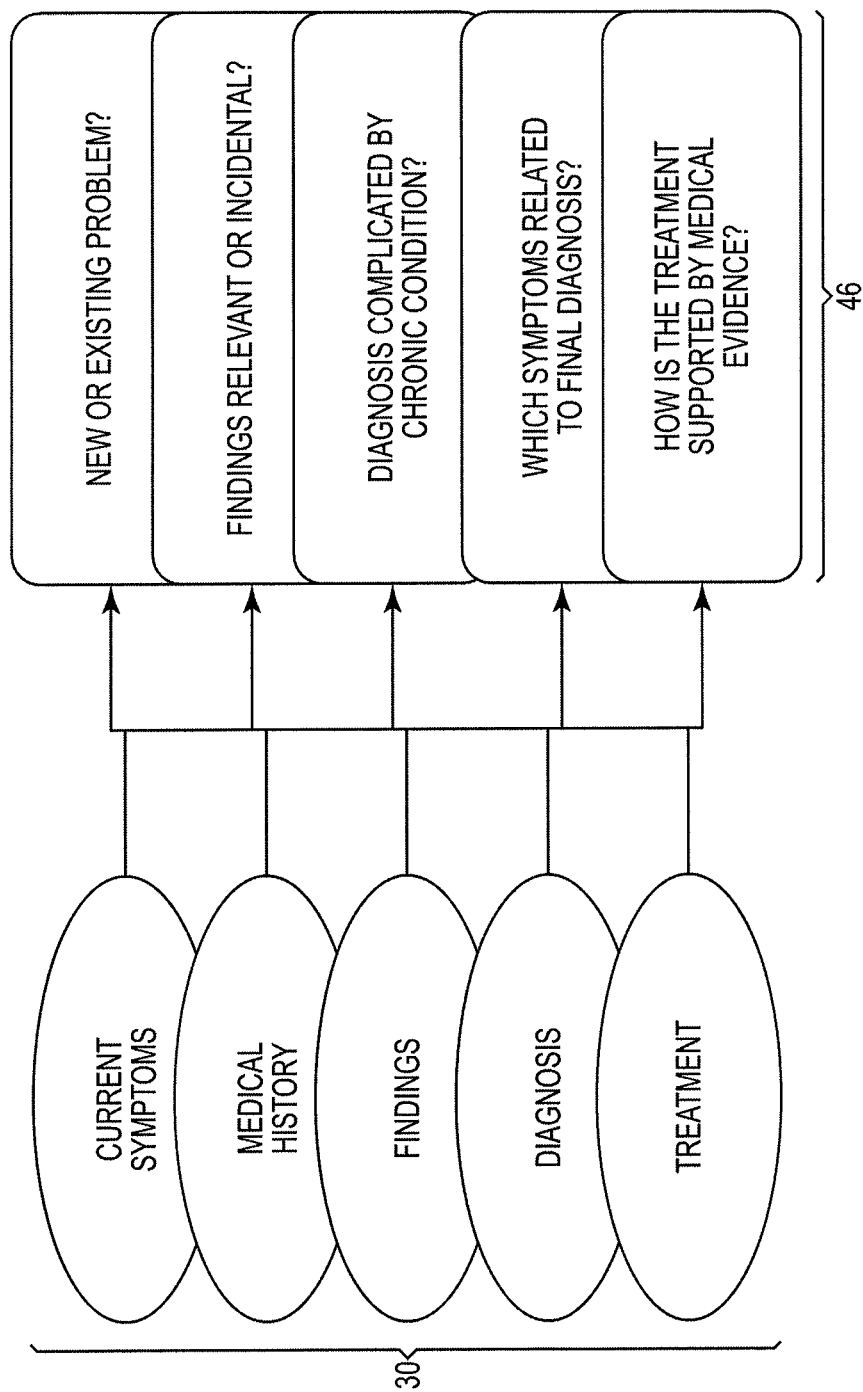
FIG. 2B is a conceptual diagram illustrating discourse analysis based on the medical record of FIG. 2A.

FIG. 2B is a conceptual diagram illustrating discourse analysis based on medical record 30 of FIG. 2A. As in FIG. 2B, discourse analysis can be applied across the entire medical record 30, including current symptoms, medical history, findings, diagnoses, and treatments, in order to generate synthesized output 46. Synthesized output 46 provides data (and answers) related to higher-level concepts and queries, such as whether the indicators relate to a new or existing problem, whether certain findings are relevant or incidental to the diagnosis or other condition of interest, whether the diagnosis is complicated by a chronic condition, which symptoms are related to the diagnosis, and how any particular treatment is supported by medical evidence. In this context, the medical record is viewed as an integrated whole, including data synthesized from all of the available information, rather than simply as a set of unrelated documents, reviewed individually or in isolation.

Discourse analysis extends the interpretation of text into multiple sentences and represents a more advanced capability of the NLP systems utilized here. While syntax and semantics analysis may be focused at the sentence or phrase level, discourse analysis can synthesize meanings from multiple sentences or paragraphs to recognize a higher level of concepts and identify (or generate) more sophisticated clinical indicators. The interpretation of the word LASIX for example, is different in a list of allergies than in a list of admitting medications, and the interpretation is also different when used in a list of discharge medications. These are all very different situations from a clinical perspective, and NLP-based CPI analysis provides the ability to understand and act on how these forms of discourse context affect interpretation of the record.

CDI Example

Figure 3:
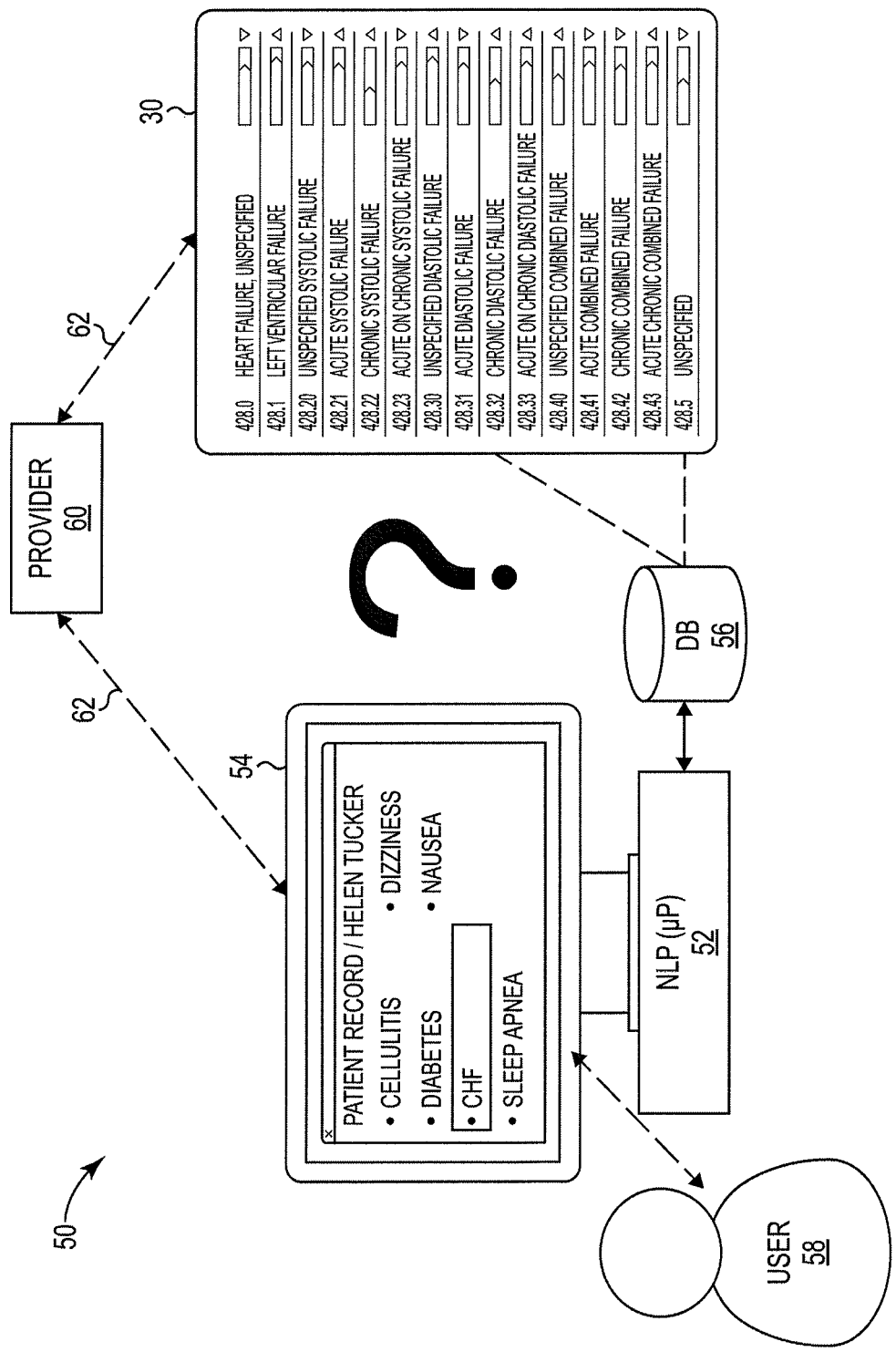
FIG. 3 is a schematic illustration of a natural language processing (NLP) based system CDI and medical record analysis system.

FIG. 3 is a schematic illustration of a natural language processing (NLP) based system 50 for medical record review, for example in the context of clinical documentation improvement (CDI), as described above. In this particular example, system 50 includes a natural language processor (NLP) or NLP program module executable on a microprocessor (µP) or other computer processor 52, in operative communication with an interactive display or other input/output (I/O) device 54 and a database (DB) or other memory 56 for storing medical record 30.

I/O device 54 takes on a variety of forms, for example a computer monitor presenting a graphical user interface (GUI) and a keyboard for alphanumeric input from user 58. Alternatively, a touch screen or other I/O device may be used. System 50, processor 52, and I/O device 54 may also be implemented on other platforms such as a mainframe computer and workstation, or using a portable digital device such as a mobile phone or tablet computer. In each of these applications system 50 utilizes network security suitable to ensure the privacy of medical records 30 and other information according to local, state and national regulations, and under additional (more stringent) organizational rules.

Memory 56 takes on a corresponding variety of forms, for example internal or removable drive, or a cloud-based network or internet storage system. In some embodiments, memory 56 also includes a non-transitory computer readable storage medium for storing computer code executable by computer processor 52. For example, the code may include an NLP based program module configured to perform the functions of system 50 and the related method steps for NLP based medical record analysis and clinical documentation improvement, as described herein.

In the particular example of FIG. 3, medical record 30 is provided for a fictitious patient, Helen Tucker. The portion of medical record 30 displayed on I/O device 54 indicates a condition of congestive heart failure (CHF), a relatively non-specific medical diagnosis. Natural language processor based analysis system 50 is utilized to perform automated case finding, clinical indicator recognition, scenario and rule analysis, marker identification, and query generation, for example utilizing a three-tier CDI information model, as described above.

Because CHF is a non-specific diagnosis, there may be a number of associated medical codes (e.g., approximately fifteen different types of heart failure, as defined in ICD-9-CM). In previous CDI processes, medical record 30 could be reviewed to recognize the corresponding documentation of non-specific CHF, but the simply presence of such a non-specific diagnostic statement likely does not provide enough information to generate an effective physician query.

With natural-language based system 50, NLP processor 52 is configured to read and interpret additional documents and other data from medical record 30 stored in database 56 in order to recognize and identify additional clinical indicators and associated contextual information. The indicators and information identified by NLP processor 52 can be utilized in a combined scenario and rules-based analysis to generate effective queries for a physician or other provider system 60 in order to verify and update medical record 30, for example internet connections, local or wide area network links, and other communications channels 62.

In some examples, NLP system 50 may be utilized as part of a clinical document improvement (CDI) initiative. In these examples, NLP processor 52 can also provide real-time processing capability, so that effective queries can be developed to prompt a physician, lab professional, pharmacy worker, or other provider 60 to verify and update medical record 30 during a patient visit or hospital stay, or during a service call at a pharmacy or other facility.

Figure 4:
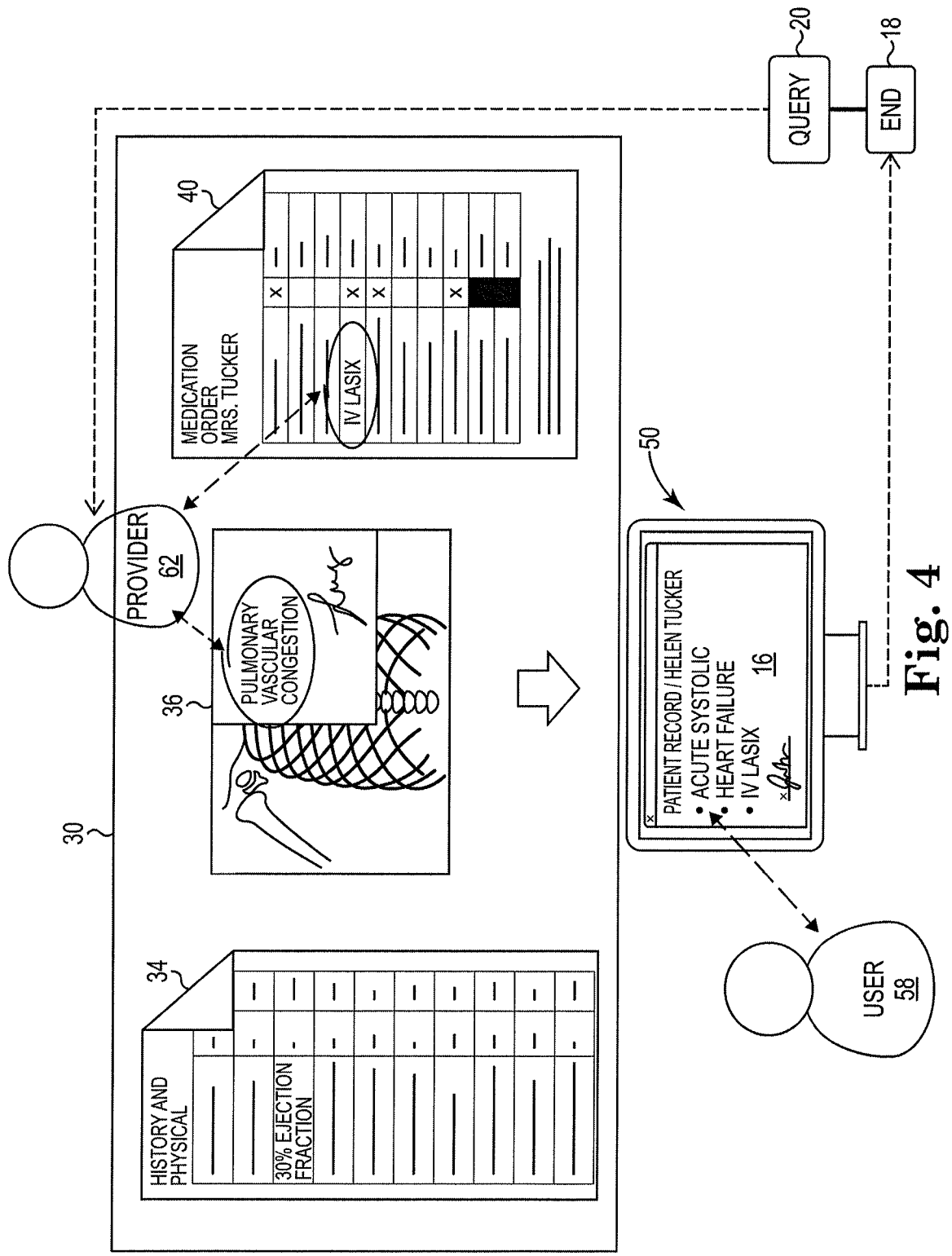
FIG. 4 is a schematic diagram illustrating utilization of the NLP based CDI system of FIG. 3.

FIG. 4 is a schematic diagram illustrating a particular utilization of natural language processing based CDI system 50 of FIG. 3. As shown in FIG. 4, three additional indicators are utilized together in order to match a particular CDI scenario.

The first indicator is documentation of 30% ejection fraction, for example as identified within current medical history documentation 34 of medical record 30, or from other physical notes taken during admission, or in the progress notes. The second additional indicator is a finding of pulmonary vascular congestion from the chest x-ray, including image data and initials or other hand-written (unstructured) data in diagnostic test documentation 36. The third additional indicator is an inpatient medication order of IV LASIX, for example in procedural notes documentation 40.

Each of these additional indicators are recognized and extracted by the NLP engine within system 50 and together trigger a business-based (pragmatic) rule or other scenario for an acute heart failure marker 16. With these indicators extracted by NLP system 50, automated case finding is substantially improved. The business rule for acute heart failure also provides the detailed evidence 18 and other information required for a physician query 20 specifically related and directed to the condition of acute heart failure, as indicated by marker 16.

In this particular example, a physician or other provider can confirm the diagnosis of acute systolic heart failure, and place an order for IV LASIX or other remedy. Such queries 20 can be communicated over the internet or by voice, text, fax, or other communications during the course of inpatient care or even at the time of an outpatient visit and the correct action can be reflected in medical record 30 in substantially real time, where it can be verified by a CDI analyst or other user 58, for example before or even during patient discharge.

In addition to better coding and other CDI improvements, an NLP engine or system 50 built with expert compliance and coding logic can also identify markers that may indicate that certain conditions were present or services were delivered, even if full documentation is not available in medical record 30. This capability to identify and flags facts based on partial information is important for new standards of care, for example ICD-10, ICD-11, and other coding and classification systems.

Compositional NLP technology also applies sophisticated models of pragmatics and discourse analysis to recognize the components that make up a particular ICD code. In addition, CDI-based business and other pragmatic rules can be triggered when partial information, nonspecific information, or clinical indicators are detected, providing medical directors, revenue cycle executives, and health information management leaders with specific, practical solutions to improve medical care and clinical documentation. These NLP-based techniques, along with rule-driven workflow and integrated physician queries, deliver a more automated and consistent CDI process for improved care management in both complex and routine patient care applications.

Figure 5:
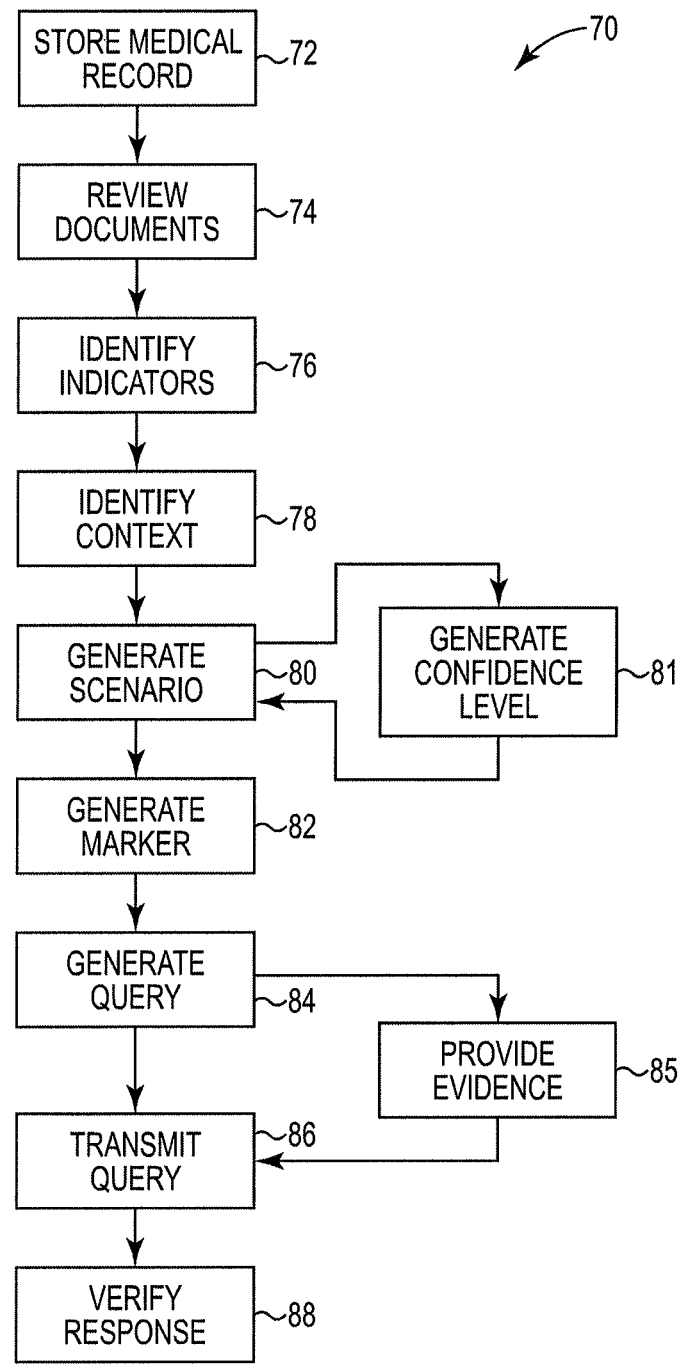
FIG. 5 is a block diagram of the method in FIG. 4.

FIG. 5 is a block diagram of a method 70 for natural language processor based medical record analysis, for example as utilized in a clinical documentation improvement system 50 as illustrated in FIGS. 3 and 4. As shown in FIG. 5, method 70 includes one or more steps including, but not limited to, storing medical records (step 72), reviewing documents (step 74), identifying indicators (step 76), identifying context (step 78), generating a scenario (step 80), generating a marker (step 82), generating a query (step 84), transmitting the query (step 86), and verifying response to the query (step 88). These steps may be performed in any order or combination, with or without any one or more additional process steps including generating confidence levels (step 81) and providing evidence related to a particular query (step 85).

Storing medical records (step 72) is performed using a medical records database or other memory system in communication with a computer processor, which executes the NLP engine or NLP software module, as described above. The medical records are typically available to both the care provider and the user of CDI system 50, for example using network connections or an internet or cloud-based server architecture.

The medical records themselves include documents and information describing or related to patient treatment, including medical history, admission, procedural, and progress notes, consultant and specialist notes, diagnostic testing. Diagnostic testing data include not only what tests were ordered, but also diagnostic results and physician including fluid workups and other laboratory analyses, x-rays and other medical images, and specialized test data such as EKG, EEG, and other specialized diagnostic data. Medical diagnoses and other statements based on the diagnostic tests can also be included, for example as made by doctors, attending physicians and other care providers, based on the lab data, images and other diagnostic results.

Document review (step 74) is performed by the NLP engine. As opposed to other techniques, the NLP engine reviews the entire medical record as a whole, rather than considering each individual document serially or in isolation. This provides for a combination of pragmatic (contextual) and discourse analysis interpretations, as described above, in order to identify specific clinical indicators (step 76) and related contextual information (step 78), including information synthesized from multiple sentences or paragraphs and across different documents to identify a higher level of more sophisticated clinical indicators and scenarios.

Scenarios are generated (step 80) by combining individual indicators with contextual information, or comparing to rule-based scenarios stored in the CDI information model. Each scenario can be assigned a confidence level (step 81), and markers can be generated based on the scenarios (step 82), for example with an overall confidence based on the highest corresponding scenario-level value or using a combined confidence level or other algorithm.

The markers indicate a medical condition that is omitted from or not completely reported in the medical record, for example a record element that is absent, where the record element indicates or is associated with a medical condition of the patient, and this medical condition is absent from the medical record, or not properly indicated on the medical record. Similarly, the markers may identify a medical condition, diagnosis, diagnosis code, or indicator of a medical condition or diagnosis that is associated with the patient, and which is absent, missing, or omitted from the medical record, or which is not found or underreported in the medical record.

The NLP engine can also be used to generate queries (step 84) describing the markers. The queries can be provided with evidence (step 85) describing one or more of the clinical indicators, the associated contextual information, or both.

Once generated, queries can be transmitted to the care provider or facility providing the patient care (step 86). Queries can be automatically set or selected for transmission by a user of the CDI system, for example using an interactive graphical interface to select one or more queries based on the underlying indicators and contextual information, or based on the confidence level of the associated scenario or marker.

After a query has been sent, the provider response can be verified (step 88) by accessing the medical record and associated documentation to determine whether an appropriate amendment, correction or update has been made. In particular, the user interface can be configured to provide traceability of the response, for example with interactive features that allow the user to "drill down" into the marker to display the associated scenario and underlying clinical indicators and associated information, and to verify that the appropriate correction has been made to the record after the query has been sent. Similar traceability features can also be provided via a provider interface at the provider facility, to enable the physician or other care provider to verify the basis for the query, and to provide an accurate, timely, and appropriate response.

While this invention has been described with reference to exemplary embodiments, it will be understood by those skilled in the art that various changes can be made and equivalents may be substituted without departing from the spirit and scope of the invention. In addition, modifications may be made to adapt the teachings of the invention to particular situations and materials without departing from the essential scope thereof. Thus, the invention is not limited to the particular examples that are disclosed herein, but encompasses all embodiments falling within the scope of the appended claims.

The invention claimed is:

1. A computer-based, natural language processing system comprising:
 a computer processor operatively coupled to an interactive display;
 a database in communication with the computer processor, the database comprising memory for storing a medical record, the medical record comprising a plurality of electronic documents relating to patient care; and
 a natural language processor module executing on the computer processor, the natural language processor module configured to:
  review the plurality of electronic documents in the medical record as a whole through a combination of semantic analysis, syntax analysis, pragmatic analysis and discourse analysis of structured and unstructured data included in the plurality of electronic documents to identify clinical indicators and associated contextual information, wherein pragmatic analysis comprises determining a document type of at least one of the plurality of electronic documents, and wherein discourse analysis comprises synthesizing meanings from multiple sentences or paragraphs across at least some of the plurality of electronic documents, wherein discourse analysis comprises synthesizing descriptions of current symptoms, vital signs, laboratory results, medication orders, medical history data, previous findings or diagnoses, and previous treatments, wherein the clinical indicators and associated contextual information are analyzed according to the document type in which the clinical indicators are identified and according to the associated contextual factors related to the clinical indicator;

compare the clinical indicators and associated contextual information to rule-based scenarios;

generate a marker based on the clinical indicators and associated contextual information, the marker identifying a record element associated with a medical condition relating to the patient care, wherein the record element is absent from the medical record, wherein the clinical indicators, rule-based scenarios and the marker are organized in separate tiers of a tiered information model; and generate a query for a service provider, the query describing the marker and provided with evidence describing at least one of the clinical indicators and associated contextual information from which the marker was generated, wherein the service provider provides the patient care;

transmit the query to the service provider;

receive a service provider response to the query; and verify the service provider response to the query, wherein verifying the service provider response to the query comprises accessing the medical record to determine whether the service provider response to the query includes an appropriate amendment, correction, or update.

2. The system of claim 1, further comprising a user interface in operative communication with the computer processor, the user interface configured to display the clinical indicators and associated contextual information.

3. The system of claim 2, wherein the user interface is further configured to display a confidence level associated with the marker, based on the clinical indicators and associated contextual information.

4. The system of claim 3, wherein the user interface is further configured to accept a user selection of the query, based on the confidence level, such that the query is transmitted to a provider of the patient care.

5. The system of claim 4, wherein the user interface is further configured to validate a response to the query, the response providing the record element in the medical record.

6. The system of claim 1, wherein the user interface provides for interactive traceability of the marker, based on interactive features that relate the marker to the scenarios, clinical indicators and associated contextual information.

7. The system of claim 1, wherein the information model is configured to generate the marker based on a combination indicators comprising different laboratory results.

8. The system of claim 1, wherein the information model is configured to generate the marker based on a combination of vital signs and textual indicators, the vital signs and textual indicators being found in different documents in the medical record.

9. The system of claim 1, wherein the information model is configured to generate the marker based on a combination of indicators comprising the structured and unstructured data in the medical record.

10. A computer implemented method for natural language processing of medical records, the method comprising:

reading a medical record from memory in operative communication with a computer system, the medical record comprising documents related to patient care;

executing a natural language processor on the computer system, the natural language processor:

reviewing a plurality of electronic documents in the medical record as a whole through a combination of semantic analysis, syntax analysis, pragmatic analysis and discourse analysis of structured and unstructured data included in the plurality of electronic documents to extract data related to the patient care and identify clinical indicators and associated contextual information, wherein pragmatic analysis comprises determining a document type of at least one of the plurality of electronic documents, and wherein discourse analysis comprises synthesizing meanings from multiple sentences or paragraphs across at least some of the plurality of electronic documents, wherein discourse analysis comprises synthesizing descriptions of current symptoms, vital signs, laboratory results, medication orders, medical history data, previous findings or diagnoses, and previous treatments, wherein the clinical indicators and associated contextual information are analyzed according to the document type in which the clinical indicators are identified and according to the associated contextual factors related to the clinical indicator;

combining the clinical indicators and associated contextual information into a rule-based scenario;

generating a marker based on the scenario, wherein the marker identifies an indication of a medical condition related to the patient care, the indication being absent from the medical record, wherein the clinical indicators, rule-based scenario and the marker are organized in separate tiers of a tiered information model;

generating a query for a service provider, the query describing the marker, wherein the service provider provides the patient care; and transmitting the query from the computer system to the service provider, the service provider providing the patient care;

receiving a service provider response to the query; and verifying the service provider response to the query, wherein verifying the service provider response to the query comprises accessing the medical record to determine whether the service provider response to the query includes an appropriate amendment, correction, or update.

11. The method of claim 10, further comprising the natural language processor providing evidence with the query, the evidence describing at least one of the clinical indicators and associated contextual information combined into the rule-based scenario.

12. The method of claim 10, further comprising the computer system receiving confirmation of the query from the service provider.

13. The method of claim 12, further comprising verification presence of the indication of the medical condition in the medical record, based on the confirmation.

14. The method of claim 10, further comprising generating a confidence level for the marker, based on the scenario.

15. The method of claim 14, further comprising receiving a user selection of the query via a graphical interface in operative communication with the computer system, the user selection based on the confidence level.

16. The method of claim 10, wherein at least one of the clinical indicators is generated from the unstructured data in the medical record, the unstructured data comprising free text.

17. The method of claim 16, wherein at least one of the clinical indicators is generated from the structured data in the medical record.

18. The method of claim 17, wherein the structured data comprise a laboratory test result in combination with a treatment code.

19. The method of claim 16, wherein the structured data comprise a medical treatment code.

* * * * *